US010729791B2

(12) United States Patent
Saint-Remy et al.

(10) Patent No.: US 10,729,791 B2
(45) Date of Patent: Aug. 4, 2020

(54) ANIMAL MODELS FOR EVALUATING PHARMACEUTICAL COMPOUNDS

(71) Applicant: ImCyse SA, Liège (BE)

(72) Inventors: Jean-Marie Saint-Remy, Grez-Doiceau (BE); Luc Vander Elst, Obaix (BE); Vincent Carlier, Enines (BE)

(73) Assignee: IMCYSE SA, Belgium (NL)

(*) Notice: Subject to any disclaimer, the term of this patent is extended or adjusted under 35 U.S.C. 154(b) by 124 days.

(21) Appl. No.: 15/151,868

(22) Filed: May 11, 2016

(65) Prior Publication Data
US 2016/0339121 A1 Nov. 24, 2016

(30) Foreign Application Priority Data

May 18, 2015 (EP) ..................................... 15167964

(51) Int. Cl.
A61K 49/00 (2006.01)
G01N 33/50 (2006.01)
A01K 67/027 (2006.01)

(52) U.S. Cl.
CPC ........ A61K 49/0008 (2013.01); A01K 67/027 (2013.01); G01N 33/5088 (2013.01); A01K 2207/10 (2013.01); A01K 2227/10 (2013.01); A01K 2267/0387 (2013.01)

(58) Field of Classification Search
CPC ................ A61K 49/00; A61K 49/0004; A61K 49/0008; A61K 2123/00; A61K 2100/00; A61K 49/001; A01K 67/027; A01K 2227/10; A01K 2267/0387; A01K 2207/10; G01N 33/5088
USPC .......... 424/1.11, 1.65, 1.69, 1.81, 1.85, 1.89, 424/9.1, 9.2; 514/1, 1.1; 530/300
See application file for complete search history.

(56) References Cited

U.S. PATENT DOCUMENTS

| 4,599,231 | A | 7/1986 | Milich et al. |
| 4,886,782 | A | 12/1989 | Good et al. |
| 5,433,948 | A | 7/1995 | Thomas et al. |
| 5,552,142 | A | 9/1996 | Thomas et al. |
| 5,589,175 | A | 12/1996 | Vahlne et al. |
| 5,633,234 | A | 5/1997 | August et al. |
| 5,736,142 | A | 4/1998 | Sette et al. |
| 5,770,202 | A | 6/1998 | Thomas et al. |
| 5,773,002 | A | 6/1998 | Thomas et al. |
| 5,863,528 | A | 1/1999 | Hawley et al. |
| 6,399,383 | B1 | 6/2002 | Apt et al. |
| 6,602,509 | B1 | 8/2003 | Saint-Remy et al. |
| 6,656,471 | B1 | 12/2003 | Sastry et al. |
| 6,759,046 | B1 | 7/2004 | Gaudernack et al. |
| 7,157,089 | B1 | 1/2007 | Mizzen et al. |
| 7,306,804 | B2 | 12/2007 | Sastry et al. |
| 7,780,882 | B2 | 8/2010 | Chang et al. |
| 8,999,346 | B2 * | 4/2015 | Saint-Remy ....... A61K 39/0011 424/185.1 |
| 9,044,507 | B2 | 6/2015 | Saint-Remy |
| 9,248,171 | B2 | 2/2016 | Saint-Remy |
| 9,249,202 | B2 * | 2/2016 | Saint-Remy ........... A61K 35/17 |
| 9,394,517 | B2 | 7/2016 | Saint-Remy |
| 9,861,661 | B2 | 1/2018 | Saint-Remy |
| 10,023,847 | B2 | 7/2018 | Saint-Remy |
| 2003/0049723 | A1 | 3/2003 | Zhang et al. |
| 2003/0104570 | A1 | 6/2003 | Cabezon Silva et al. |
| 2003/0129205 | A1 | 7/2003 | Saint-Remy et al. |
| 2003/0152581 | A1 | 8/2003 | Saint-Remy et al. |
| 2004/0077045 | A1 | 4/2004 | Zhang et al. |
| 2005/0032039 | A1 | 2/2005 | Sastry et al. |
| 2005/0107256 | A1 | 5/2005 | Barnwell et al. |
| 2005/0196386 | A1 | 9/2005 | Blazar et al. |
| 2005/0202044 | A1 | 9/2005 | Mizzen et al. |
| 2006/0182763 | A1 | 8/2006 | Kim et al. |
| 2006/0211091 | A1 | 9/2006 | Zhang et al. |
| 2006/0216301 | A1 | 9/2006 | Tahara et al. |
| 2006/0269561 | A1 | 11/2006 | Paterson et al. |
| 2007/0160620 | A1 | 7/2007 | Mizzen et al. |
| 2007/0184023 | A1 | 8/2007 | Rasmussen et al. |
| 2008/0176247 | A1 | 7/2008 | Chou et al. |
| 2009/0012004 | A1 | 1/2009 | Sette et al. |
| 2010/0033088 | A1 | 2/2010 | Hwang et al. |
| 2010/0068193 | A1 | 3/2010 | Brunsvig et al. |
| 2010/0183652 | A1 | 7/2010 | Page et al. |
| 2010/0203083 | A1 | 8/2010 | Lux et al. |
| 2010/0303866 | A1 | 12/2010 | Saint-Remy |
| 2010/0330088 | A1 | 12/2010 | Sai Nt-Remy |
| 2011/0002903 | A1 | 1/2011 | Saint-Remy |

(Continued)

FOREIGN PATENT DOCUMENTS

JP 2004147649 A 5/2004
WO WO-8504103 A1 9/1985

(Continued)

OTHER PUBLICATIONS

EP Search Report for EP 15167964 ("Novel Animal models for evaluating pharmaceutical compounds", Applicant: Imcyse SA), dated Oct. 21, 2016, 7 pages.

(Continued)

Primary Examiner — D. L. Jones
(74) Attorney, Agent, or Firm — Nixon & Vanderhye, P.C.

(57) ABSTRACT

The application relates to methods for determining a parameter such as toxicity and pharmacokinetic behavior for a pharmaceutical compound against a disease or disorder. The test animals being used are non-human animals not suffering from or is not showing symptoms or signs of the disorder and which do not provoke an immune response against said pharmaceutical compound. These animals are obtainable by administration of a peptide comprising an oxidoreductase motif further comprising an NKT peptide epitope or an MHC class II T cell epitope of said pharmaceutical compound, wherein said motif and said epitope are separated by a linker of between 0 and 4 amino acids.

18 Claims, No Drawings
Specification includes a Sequence Listing.

(56) References Cited

U.S. PATENT DOCUMENTS

| | | |
|---|---|---|
| 2011/0110964 A1 | 5/2011 | Saint-Remy |
| 2011/0111395 A1 | 5/2011 | Saint-Remy |
| 2011/0111502 A1 | 5/2011 | Saint-Remy |
| 2012/0009678 A1 | 1/2012 | Saint-Remy |
| 2013/0095133 A1* | 4/2013 | Klatzmann .......... A61K 39/145 424/192.1 |
| 2013/0259885 A1 | 10/2013 | Saint-Remy |
| 2014/0370044 A1 | 12/2014 | Saint-Remy |
| 2014/0377299 A1 | 12/2014 | Saint-Remy |
| 2015/0110821 A1 | 4/2015 | Saint-Remy |
| 2015/0216901 A1 | 8/2015 | Saint-Remy |
| 2016/0091492 A1 | 3/2016 | Saint-Remy et al. |
| 2016/0108103 A1 | 4/2016 | Saint-Remy |
| 2016/0194367 A1 | 7/2016 | Saint-Remy |
| 2016/0250255 A1 | 9/2016 | Saint-Remy et al. |
| 2017/0100466 A1 | 4/2017 | Saint-Remy |
| 2018/0228912 A1 | 8/2018 | Saint-Remy et al. |
| 2018/0258154 A1 | 9/2018 | Saint-Remy et al. |
| 2018/0346887 A1 | 12/2018 | Saint-Remy |
| 2019/0106477 A1 | 4/2019 | Vander |

FOREIGN PATENT DOCUMENTS

| | | |
|---|---|---|
| WO | WO-9205800 A1 | 4/1992 |
| WO | WO-9308279 A1 | 4/1993 |
| WO | WO-9405790 A1 | 3/1994 |
| WO | WO-9740852 A1 | 11/1997 |
| WO | WO-9958552 A2 | 11/1999 |
| WO | WO-0029008 A2 | 5/2000 |
| WO | WO-0155393 A2 | 8/2001 |
| WO | WO-0170263 A1 | 9/2001 |
| WO | WO-0200892 A1 | 1/2002 |
| WO | WO-02095051 A2 | 11/2002 |
| WO | WO-02097070 A1 | 12/2002 |
| WO | WO-03072731 A2 | 9/2003 |
| WO | WO-2004018667 A1 | 3/2004 |
| WO | WO-2004024766 A1 | 3/2004 |
| WO | WO-2005012502 A2 | 2/2005 |
| WO | WO-2005039613 A1 | 5/2005 |
| WO | WO-2005042575 A2 | 5/2005 |
| WO | WO-2005086781 A2 | 9/2005 |
| WO | WO-2006009920 A2 | 1/2006 |
| WO | WO-2006059529 A1 | 6/2006 |
| WO | WO-2007027954 A2 | 3/2007 |
| WO | WO-2007104715 A2 | 9/2007 |
| WO | WO-2007135684 A2 | 11/2007 |
| WO | WO2008/017517 | 2/2008 |
| WO | WO-2009042215 A3 | 4/2009 |
| WO | WO2009/101205 | 8/2009 |
| WO | WO2009/101206 | 8/2009 |
| WO | WO2009/101208 | 8/2009 |
| WO | WO-2009100505 A1 | 8/2009 |
| WO | WO-2009101201 A2 | 8/2009 |
| WO | WO-2009101204 A2 | 8/2009 |
| WO | WO-2009101207 A1 | 8/2009 |
| WO | WO-2009106073 A2 | 9/2009 |
| WO | WO-2010037395 A2 | 4/2010 |
| WO | WO-2010115046 A2 | 10/2010 |
| WO | WO 2012/069568 | 5/2012 |
| WO | WO 2013/121296 | 8/2013 |
| WO | WO-2013113076 A1 | 8/2013 |
| WO | WO-2014191432 A1 | 12/2014 |
| WO | WO-2015063176 A1 | 5/2015 |
| WO | WO-2016059236 A1 | 4/2016 |

OTHER PUBLICATIONS

Carlier et al., "Increased Synapse Formation Obtained by T Cell Epitopes Containing a CxxC Motif in Flanking Residues Convert CD4+ T Cells into Cytolytic Effectors", Plos One, vol. 7, No. 10, Jan. 1, 2012, p. e45366.

De Groot et al., "Immunogenicity of Protein Therapeutics", Trends in Immunology, vol. 28, No. 11, Oct. 25, 2007, pp. 482-490.

Zhang et al., "Preclinical Experimental Models of Drug Metabolism and Disposition in Drug Discovery and Development", Acta Pharmaceutica Sinica B, vol. 2, No. 6, Dec. 1, 2012, pp. 549-561.

Jiang et al., "Protection by the Gross Saponins of Tribulus Terrestris Against Cerebral Ischemic Injury in Rats Involves the NF-κB Pathway", Acta Pharmaceutica Sinica B, 2011, 1 (1), pp. 21-26.

Abrahimians et al., "MHC class II-restricted epitopes containing an oxidoreductase activity prompt CD4+ T cells with apoptosis-inducing properties," Frontiers in Immunology, vol. 6, 2 (2015), pp. 1-5.

Aleksza et al., "Altered cytokine expression of peripheral blood lymphocytes in polymyositis and dermatomyositis," (2005) Ann. Rheum. Dis. 64, 1485-1489.

Aley & Gillin, "Giardia lambiia: post-translational processing and status of exposed cysteine residues in TSA 417, a variable surface antigen" (1993) Exp Parasitol. 77, 295-305.

Apostolou et al., "Evidence for two subgroups of CD4-CD8-NKT cells with distinct TCR alpha beta repertoires and differential distribution in lymphoid tissues," J Immunol. 165(5):2481-90 (2000).

Appella et al., "Analysis of the structure of naturally processed peptides bound by class I and class II major histocompatibility complex molecules." EXS. (1995) 73:105-19.

Arunachalam et al., "Enzymatic reduction of disulfide bonds in lysosomes: Characterization of a Gamma-interferon-inducible lysosomal thiol reductase (GILT)," (2000) Proc. Natl. Acad. Sci USA, vol. 97, No. 2, 745-750.

Ascherio et al., "Environmental factors in multiple sclerosis," Expert Rev Neurother. 13(12 S):3-9 (2013).

Azoury-Ziadeh et al., "T-Helper Epitopes Identified Within the E6 Transforming Protein of Cervical Cancer-Associated Human Papillomavirus Type 16," Viral Immunology, 1999, 12(4): 297-312.

Balato et al., "Natural killer T cells: An unconventional T-cell subset with diverse effector and regulatory functions," Journal of Investigative Dermatology 129: 1628-1642 (2009).

Batten et al., "Immune response to stem cells and strategies to induce tolerance," (2007) Phil. Trans. R. Soc. B 362, 1343-1356.

Boisgerault et al., "Differential roles of direct and indirect allorecognition pathways in the rejection of skin and corneal transplants," (2009) Transplantation 87(1): 16-23.

Bolivar et al., "Molecular cloning of a zinc finger autoantigen transiently associated with interphase nucleolus and mitotic centromeres and midbodies. Orthologous proteins with nine CXXC motifs highly conserved form nematodes to humans," J. Biol, Chem., vol. 274, (1999), pp. 36456-36464.

Bower et al., "Two Members of the Thioredoxin-h Family Interact with the Kinase Domain of a Brassica S Locus Receptor Kinase," (1996) The plant cell, vol. 8, 1641-1650.

Braun et al., "Acute rejection in the absence of cognate recognition of allograft by T cells," J. Immunol., vol. 166, No. 8, (2001), pp. 4879-4883.

Brinks et al., "Immunogenicity of Therapeutic Proteins: The Use of Animal Models," Pharm Res (2011) 28:2379-2385.

Brinster et al., "Bone Marrow-Derived Dendritic Cells Reverse the Anergic State of CD4+CD25+T Cells without Reversing Their Suppressive Function," (2005), The Journal of Immunology 175:7332-7340.

Brinster et al., "Costimulatory effects of IL-1 on the expansion/differentiation of CD4+CD25+Foxp3+and CD4+CD25+Foxp3—T cells," J. Leukoc. Biol., vol. 84, (2008), pp. 480-487.

Cao et al., "Prevention of gene transfer-induced inhibitor formation by nasal administration of human F.IX T cell epitope in a murine model of hemophilia B.," Blood, vol. 104(11), (2004), pp. 121A-122A.

Capon et al., "The CD4-gp120 Interaction and Aids Pathogenesis," (1991) Ann. Rev. Immunol 9, 649-678.

Caro-Aguilar et al., "Chimeric epitopes delivered by polymeric synthetic linear peptides induce I protective immunity to malaria," Microbes Infect. 7:1324-1337 (2005).

Carlier et al., "Increased Synapse Formation Obtained by T cell Epitopes Containing a CxxC Motif in Flanking Residues Convert CD4+ T Cells into Cytolytic Effectors," PLOS One, Oct. 2012, vol. 7, Issue 10, e45366, pp. 1-16.

(56) References Cited

OTHER PUBLICATIONS

Carlier et al., "Control of asthma by in vitro-induced allergen-specific regulatory T cells in the mouse," Munksgaard Allergy. 62(Suppl 83):555 (Abstract 1 616) (2007).
Castano et al., "Peptide binding and presentation by mouse CD1," Science 269: 223-226 (1995).
Cavone et al., "Long-term suppression of EAE relapses by pharmacological impairment of epitope spreading," Br J Pharmacol 171 (6):1501-9 (2014).
Celis et al., "Induction of anti-tumor cytotoxic T lymphocytes in normal humans using primary cultures and synthetic peptide epitopes," Proc Natl Acad Sci USA. Mar. 15, 1994;91 (6):2105-9.
Chen et al., "Induction of dominant transplanation tolerance by an altered peptide ligand of the male antigen Dby," (2004) J Clin. Invest. 113(12), 1754-1762.
Chen et al., "Glucocorticoid amplifies Il-2-dependent expansion of functional FoxP3+CD4+CD25+ T regulatory cells in vivo and enhances their capacity to suppress EAE," (2006) Eur. J. Immunol. 36, 2139-2149.
Chuanlin ed., Molecular Immunology, Fudan University Press, Shanghai Medical College Press; publication date: May 2001; pp. 428-429, 433-436 (English language translation provided) (15 pages).
Corthay et al., "CD4+ T Cells Cooperate with Macrophages for Specific Elimination of MHC Class II-Negative Cancer Cells," (2007) Adv Exp Med Biol. 590, 195-208.
Cotton et al., "Oxidative inhibition of human soluble catechol-O-methyltransferase," (2004) Biol. Chem. vol. 279: 23710-718.
Credo Reference, (2012)(cited by Examiner—best available copy).
Crellin et al., "Altered activation of AKT is required for the suppressive function of human CD4+CD25+ T regulatory cells," Blood 1 09(5):2014-2022 (2007).
Crompton et al., "Advances and challenges in malaria vaccine development," The Journal of Clinic Investigation, 2010, 120, pp. 4168-4178.
Davids et al., A new family of giardial cysteine-rich non-VSP protein genes and a novel cyst protein, PLOS. One. vol. 1, (2006), e44.
Davis et al., "Interrogating the repertoire: broadening the scope of peptide-MHC multimer analysis," Nature Rev. Immunology, (2011), 11, 551-558.
De La Cruz et al., "The immunologic significance of variation within malaria circumsporozoite protein sequences," J. Immunol., vol. 142, (1989), pp. 3568-3575.
Desmetz et al., "Proteomics-Based Identification of HSP60 as a Tumor-Associated Antigen in Early Stage Breast Cancer and Ductal Carcinoma in situ," Journal of Proteome Research (2008), 7, 3830-3837.
Dobrzanski, "Expanding roles for CD4T cells and their subpopulations in tumor immunity and therapy," Frontiers in Oncology, Mar. 2013, vol. 3, Article 63, pp. 1-19.
Dobrzynski et al., "Prevention of cytotoxic T lymphocyte responses to factor IX-expressing hepatocytes by gene transfer-induced regulatory T cells," Proc. Natl. Acad. Sci. U.S.A., vol. 103, (2006), pp. 4592-4597.
Eberl et al., "Tissue-specific segregation of CD1d-dependent and CD1d-independent NK T cells," J. Immunol., vol. 162, (1999), pp. 6410-6419.
Facktor et al., "Hypersensitivity to tetanus toxoid," J Allergy Clin Immunol. Jul. 1973;52(1): 1-12.
Fan et al., "Co-immunization of BALB/c mice with recombinant immunogens containing G fragment and chimeric CTL epitope of respiratory syncytial virus induces enhanced cellular immunity and high level of antibody response," (2005) Vaccine 23, 4453-4461.
Fomenko et al., "Identity and functions of CxxC-derived motifs," Biochemistry, vol. 42, (2003), pp. 11214-11225.
Francois et al., "The CD4+ T-Cell Response of Melanoma Patients to a MAGE-A3 Peptide Vaccine Involves Potential Regulatory T Cells," Cancer Res. 69(10):4335-4345 (2009).
Frankel et al., "Characterization of diphtheria fusion proteins targeted to the human interleukin-3 receptor," Protein Eng. 13(8):575-81 (2000).
Freeman (Molecular Cell Biology, 4th Edition, Lodish et al., Eds, New York, 2000, section 6.3, "Viruses: Structure, Function, and Uses").
Ge et al., "An hsp 70 fusion protein vaccine potentiates the immune response against Japanese encephalitis virus," (2007) Arch. Viral 152, 125-135.
Geluk et al., "HLA-DR binding analysis of peptides from islet antigens in IDDM," Diabetes, vol. 47, (1998), pp. 1594-1601.
GenBank AA5961 0.1, 1995, p. 1.
GenBank AAA58655.1, 1994, p. 1.
GenBank FPAA051928, 1997, p. 1.
GenBank M77349.1—Skonier et al., "Human transforming growth factor-beta induced gene product (BIGH3) mRNA, complete cds," Jan. 14, 1995 (3 pages).
GenPept PDB 5GSB_A, 2017, pp. 1-2.
Gentile et al., "Thyroglobulin as an autoantigen: what can we learn about immunopathogenicity from the correlation of antigenic properties with protein structure?," (2004) Immunol 112 13-25.
Girardi et al., "Structure of an alpha-helical peptide and lipopeptide bound to the nonclassical major histocompatibility complex (MHC) class I molecule CD1 d," J Biol Chem. 291 (20):1 0677-83 (2016).
Gross et al., "Simple conditioning with monospecific CD4+CD25+ regulatory T cells for bone marrow engraftment and tolerance to multiple gene products," Blood, vol. 108, No. 6, (2006), pp. 1841-1848.
Grossman et al., "Differential expression of granzymes A and B in human cytotoxic lymphocyte subsets and T regulatory cells," Blood, vol. 104, (2004), pp. 2840-2848.
Haque, "Cysteinylation of MHC Class II Ligands: Peptide Endocytosis and Reduction Within APC Influences T Cell Recognition. sup.1," (2001) J. Immunol. 166, 4543-4551.
Harris et al., "Prediction of murine MHC class I epitopes in a major house dust mite allergen and induction of T1-type CD8+ T cell responses," (1997) Int. Immunol., vol. 9, No. 2, 273-280.
Haveman et al., "Induction and capture of CD4+ cytotoxic adenoviral specific T-cells in response to pan-DR binding adenoviral epitopes toward immunotherapy," Blood, vol. 106, (2005), Abstract 3238.
Haveman et al., "Novel pan-DR-binding T cell epitopes of adenovirus induce pro-inflammatory cytokines and chemokines in healthy donors," Int Immunol. 18(11):1521-1529 (2006).
Heemskerk et al., "Adenovirus-Specific CD4.sup.+ T Cell Clones Recognizing Endogenous Antigen Inhibit Viral Replication in Vitro through Cognate Interaction," The Journal of Immunology (2006); 177:8851-8859.
Ho et al., "CD4(−)CD8alphaalpha subset of CD1d-restricted NKT cells controls T cell expansion," J Immunol. 172(12):7350-8 (2004).
Hohn et al., "CD4+ tumor-infiltrating lymphocytes in cervical cancer recognize HLA-DR-restricted peptides provided by human papillomavirus-E7," J. Immunol., vol. 163, (1999), pp. 5715-5722.
Hori et al., "Control of regulatory T cell development by the transcription factor Foxp3," Science, vol. 299, (2003), pp. 1057-1061.
Hsu et al., "Assessing computational amino acid—turn propensities with a phage-displayed combinatorial library and directed evolution," Structure, (2006), vol. 14, pp. 1499-1510.
Iqbalsyah et al., "The CXXC motif at the N terminus of an .alpha.-helical peptide," (2006) Protein Sci. 15, 1945-1950.
Ise et al., "Naive CD4+ T cells exhibit distinct expression patterns in cytokines and cell surface molecules on their primary responses to varying doses of antigen," J. Immunol., vol. 168, (2002), pp. 3242-3250.
James et al., "HY peptides modulate transplantation responses to skin allografts," Int Immunol. 14(11):1333-1342 (2002).
Janeway et al., Immunobiology, 3rd edition, Garland Press Inc., 1997, p. G: 11.
Janssens et al., "CD4+ CD25+ T Cells Lyse Antigen-Presenting B Cells by Fas-Fas Ligand Interaction in an Epitope-Specific Manner. sup.1," (2003) J. Immunol. 171, 4604-4612.

(56) References Cited

OTHER PUBLICATIONS

Jensen, "Acidification and Disulfide Reduction Can be Sufficient to Allow Intact Proteins to Bind MHC," (1993) J. Immunol. 150, No. 8, 3347-3356.
Joffre et al., "Induction of antigen-specific tolerance to bone marrow allografts with CD4+CD25+ T lymphocytes," Blood, vol. 103, No. 11, (2004), pp. 4216-4221.
Karin et al., "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production," J Exp Med. Dec. 1, 1994;180(6):2227-37.
Kasprowicz et al., "Tracking of Peptide-Specific CD4+ T-Cell Responses After and Acute Resolving Viral Infection: a Study of Parovirus 819," Journal of Virology, Nov. 2006, vol. 80, No. 22, pp. 11209-11217.
Khare et al., "HLA class II transgenic mice authenticate restriction of myelin oligodendrocyte glycoprotein-specific immune response implicated in multiple sclerosis pathogenesis," (2003) Int. Immunol. 15, No. 4, 535-546.
Klebanoff et al.,"Therapeutic cancer vaccines: are we there yet?" Immunol. Rev. (2011), 239: 27-44.
Kumar et al., "Twins and endocrinology," Indian J Endocrinol Metab. Nov. 2014;18(Suppl 1):S48-52. doi: 10.4103/2230-8210. 145074.
Lewin et al., "Effects of substitutions in the CXXC active-site motif of the extracytoplasmic hioredoxin ResA," Biochem. J. (2008), 414, 81-91.
Li et al., "Twisting immune responses for allogeneic stem cell therapy," (2009) World J Stem Cells 1(1), 30-35.
Li Pira et al., "High throughput T epitope mapping and vaccine development," The Journal of Biomedicine and Technology, (2010), vol. 2010, 12 pages.
Lindqvist et al., "Both CD4+ FoxP3+ and CD4+ FoxP3− T cells from patients with B-cell malignancy express cytolytic markers and kill autologous leukaemic B cells in vitro," Immunology 133:296-306 (2011).
Louis et al., "Contrasting CD25hiCD4+ T cells/Fox3 patterns in chronic rejection and operational drug-free tolerance," Transplantation, vol. 81, (2006), pp. 398-407.
Mach et al., "Regulation of MHC Class II Genes: Lessons from a Disease," (1996) Ann. Rev. Immunol. 14, 301-331.
Maeda et al., "CD1d-independent NKT cells in beta 2-microglobulin-deficient mice have hybrid phenotype and function of NK and T cells," J. Immunol., vol. 172, (2004), pp. 6115-6122.
Maekawa et al., "Evidence for a Domain-Swapped CD4 Dimer as the Coreceptor for Binding to Class II MHC," (2006) J. Immunol. 176(11), 6873-6878.
Markovic-Plese et al., "T cell recognition of immunodominant and cryptic proteolipid protein epitopes in humans," J Immunol. 155(2):982-92 (1995) (12 pages).
Marti et al., "Conformationally Correct Expression of Membrane-Anchored Toxoplasma gondii SAG1 in the Primitive Protozoan Giardia duodenalis," Infection and Immunity, vol. 70, No. 2, Feb. 2002, p. 1014-1016.
Massilamany et al., "Detection of autoreactive CD4 T cells using major histocompatibility complex class II dextramers," BMC Immunology, (2011), 12:40.
Matsuda et al., "CD1 d-reslricted iNKT cells, the 'Swiss-Army Knife' of the immune system," Current Opinion in Immunology, vol. 20, No. 3, Jun. 1, 2008, pp. 358-368.
Matthias et al, "Disulfide exchange in domain 2 of CD4 is required for entry of HIV-1," (2002) Nature Immunol 3, No. 8, 727-732.
Maynard et al., "Regulatory T cells expressing interleukin 10 develop from Foxp3+ and Foxp3− precursor cells in the absence of interleukin 10," Nat. Immunol., vol. 8, (2007), pp. 931-941.
MedlinePlus Medical Dictionary (Merriam Webster, Inc., 2017).
Merkler et al., "Myelin oligodendrocyte glycoprotein-induced experimental autoimmune encephalomyelitis in the common marmoset reflects the immunopathology of pattern II multiple sclerosis lesions," Multiple Sclerosis 12:369-374 (2006).
Moldovan et al., "CD4 Dimers Constitute the Functional Component Required for T Cell Activation," The Journal of Immunology (2002), 169:6261-6268.
Nepom, "MHC class II tetramers," The Journal of Immunology, (2012), 188, 2477-2482.
Nielsen et al., "Quantitative Predictions of Peptide Binding to Any HLA-DR Molecule of Known Sequence: NetMHCIIpan," PLOS Comp. Biol., 2008 4(7): 4(7): e1000107.
Ochoa-Garay et al., "The Ability of Peptides to Induce Cytotoxic T Cells in Vivo Does Not Strongly Correlate With Their Affinity for the $H-2L^d$ Molecule: Implications for Vaccine Design and Immunotherapy," Mol Immunol (1997) 34(3):273-81.
Okubo et al., "Analysis of HLA-DRB1 0901-binding HPV-16 E7 helper T cell epitopel," (2004) J Obstet Gynaecol Res. 30(2), 120-129.
Oliviera et al., "Insights into the Specificity of Thioredoxin Reductase—Thioredoxin Interactions. A Structural and Functional Investigation of the Yeast Thioredoxin System," (2010) Biochemistry 49, 3317-3326.
Papanastasiou et al. "Primary structure and biochemical properties of a variant-specific surface protein of Giardia," Molecular and Biochemical Parasitology 86 (1997) 13-27.
Park et al., "Redox Regulation Facilitates Optimal Peptide Selection by MHC Class I during Antigen Processing," Cell, (2006), 127:369-382.
Peterson, "Regulatory T-cells, diverse phenotypes integral to immune homeostasis and suppression," Toxic Path. 40(2):186-204 (2012).
Printout from NetM HCIIpan Server—prediction results dated Sep. 26, 2018, one page.
Qin et al., "Fusion protein of CDR mimetic peptide with Fc inhibit TNF-alpha induced cytotoxicity," Mol. Immunol., vol. 43, (2006), pp. 660-666.
Quintana et al., "Epitope spreading as an early pathogenic event in pediatric multiple sclerosis," Neurology 83(24):2219-26 (2014).
Rammensee et al., "MHC Ligands and Peptide Motifs," 1997, Springer, New York & Austin, Texas, USA, p. 317.
Rancaniello, "How many viruses on earth?" Virology Blog (2013), http://www.virology.ws/2013/09/06/how-many-viruses-on-earth/.
Reznik et al., "Indirect Allorecognition of Mismatched Donor HLA Class II Peptides in Lung Transplant Recipients with Bronchiolitis Obliterans Syndrome," 2001, Am. J. Transpl. vol. 1: 228-235.
Robinson, Vaccine Protocol (Humana Press, 2003, Totowa, NJ, Ed. Andrew Robinson, Michael J. Hudson and Martin P. Cranage, pp. 121-123).
Roep et al., "The problems and promises of research into human immunology and autoimmune disease," (2012) Nature Med 18(1) 48-53.
Roopenian et al., "The immunogenomics of minor histocompatibility antigens," Immunol. Rev., vol. 190, (2002), pp. 86-94.
Roper et al., "SARS vaccines: where are we?", 2009, Expert Review of Vaccines, vol. 8, pp. 887-898.
Saez-Borderias et al, "Expression and function of NKG2D in CD4+ T cells specific for human cytomegalovirus," Eur. J. Immunol., vol. 36, (2006), pp. 3198-3206.
Santin et al., "Human Papillomavirus Type 16 and 18 E7-Pulsed Dendritic Cell Vaccination of Stage IB or IIA Cervical Cancer Patients: a Phase I Escalating-Dose Trial," (2008) J. Virol. 82, No. 4, 1968-1979.
Savoldo et al., "Generation of EBV-Specific CD4+ Cytotoxic T Cells from Virus Naive Individuals.sup.1," (2002) J Immunol. 168(2), 909-918.
Schrieber et al., "Tumor immunogenicity and responsiveness to cancer vaccine therapy: The state of the art," Seminar. Immunol. 22:105-112, (2010).
Schultz et al., "A MAGE-A3 Peptide Presented by HLA-DP4 Is Recognized on Tumor Cells by CD4+ Cytolytic T Lymphocytes1," Cancer Research 60, 6272-6275, Nov. 16, 2000.
Sette et al., "HLA supertypes and supermotifs: a functional perspective on HLA polymorphism," (1998) Curr Opinion Immunol. 10, 478-482.

(56) References Cited

OTHER PUBLICATIONS

Sette et al., "Epitope-based vaccines: an update on epitope identification, vaccine design and delivery," 2003, Current Opinion in Immunology, vol. 15, pp. 461-470.
Shi et al., "A novel plasma membrane-bound thioredoxin from soybean," (1996) Plant Mol. Biol. 32, 653-662 (Abstract).
Stenstrom et al., "Natural killer T-cell populations in C57BL/6 and NK1.1 congenic BALB.NK mice—a novel thymic subset defined by BALB.NK mice," Immunology, vol. 114, (2005), pp. 336-345.
Straub et al., "Allelic variation in GAD1 (GAD67) is associated with schizophrenia and influences cortical function and gene expression," Molecular Psychiatry (2007) 12, 854-869.
Sundar et al., "Generation of Epstein-Bar virus antigen-specific suppressor T cells in vitro," Int. J. Cancer, vol. 35, (1985), pp. 351-357.
Taylor et al., "T regulatory cells and allergy," Microbes and Infection, vol. 7, (2005), pp. 1049-1055.
Texier et al., "On the diversity and heterogeneity of H-2$^d$-restricted determinants and T cell epitopes from the major bee venom allergen," (1999) Int Immunol. 11, 1313-1325.
Thomson et al., "Targeting a Polyepitope Protein Incorporating Multiple Class II-Restricted Viral Epitopes to the Secretory/Endocytic Pathway Facilitates Immune Recognition by CD4+ Cytotoxic T Lymphocytes: a Novel Approach to Vaccine Design," J. of Virol, 1998, 72(3):2246-2252.
Tindle et al., "A "public" T-helper epitope of the E7 transforming protein of human papillomavirus 16 provides cognate help for several E7 B-cell epitopes from cervical cancer-associated human papillomavirus genotypes," (1991) Proc Natl. Acad. Sci 88, 5887-5891.
Tisch et al., "Antigen-specific immunotherapy: Is it a real possibility to combat T-cell-mediated autoimmunity?" PNAS 91: 437-438, (1994).
Toyokawa et al., "Relative Contribution of Direct and Indirect Allorecognition in Developing Tolerance After Liver Transplantation," 2008 Liver Transpl. 14(3) 346-357.
Tsuji et al., "Antigen-specific, CD4+CD25+ regulatory T cell clones induced in Peyer's patches," Int. Immunol., vol. 15, (2003), pp. 525-534.
U.S. Appl. No. 16/091,549, unpublished application. (date not provided).
UniProt P01906.2, 2017, p. 1-6.
UniProt O15523.2, 2017, pp. 1-7.
Voo et al., "Functional characterization of EBV-encoded nuclear antigen 1-specific CD4+ helper and regulatory T cells elicited by in vitro peptide stimulation," Cancer Res., vol. 65, (2005), pp. 1577-1586.
Wang et al., "Generation and characterization of HLA-A*2.1 restricted and Prostein 31-39 specific NKT cell lines," Acta Academiae Medicine Militaris Tertiae. 28(16):1652-1655 (2006) (English language translation provided) (11 pages).
Wang, "Immune suppression by tumor-specific CD4+ regulatory T-cells in cancer," Semin. Cancer Biol., vol. 16, (2006), pp. 73-79.
Weissert et al., "MHC Class II-Regulated Central Nervous System Autoaggression and T Cell Responses in Peripheral Lymphoid Tissues Are Dissociated in Myelin Oligodendrocyte Glycoprotein-Induced Experimental Autoimmune Encephalomyelitis.sup.1," (2001) J. Immunol. 166, 7588-7599.
Wekerle et al., "Autoimmunity's next top models," (2012) Nature Med. 18(1), 66-70.
Wiker et al., "Cloning, expression and significance of MPT53 for identification of secreted proteins of *Mycobacterium tuberculosis*," Microb. Pathog., vol. 26, (1999), pp. 207-219.
Wobus et al., "Embryonic Stem Cells: Prospects for Developmental Biology and Cell Therapy," (2005) Physiol Rev 85: 635-678.
Wood et al., "Regulatory T cells in Transplantation tolerance," Nat. Rev. Immunol., vol. 3, (2003), pp. 199-210.
Wooldridge et al., "Tricks with tetramers: how to get the most from multimeric peptide-MHC," Immunology, 2009, 126(2):147-64.

Written Description Training Materials, Revision 1, Mar. 25, 2008, U.S. Patent and Trademark Office.
Wu et al., "Engineering an intracellular pathway for major histocompatibility complex class II presentation of antigens," (1995) Proc. Natl. Acad. Sci. 92, 11671-11675.
Zeng at al., "Crystal structure of mouse CD1: An MHC-like fold with a large hydrophobic binding groove," Science 277: 339-345 (1997).
Zhang et al., "A MAGE-3 Peptide Presented by HLA-DR1 to CD4+ T Cells That Were Isolated from a Melanoma Patient Vaccinated with a MAGE-3 Protein," J Immunol. 171:219-225 (2003).
Zhao et al., "Activated CD4+CD25+ T cells selectively kill B Lymphocytes," Blood, vol. 107, No. 10; pp. 3925-3932; May 15, 2006.
Abrahimians, E. M., et al., "Thioreductase-Containing Epitopes Inhibit the Development of Type 1 Diabetes in the NOD Mouse Model," Frontiers in Immunology 7(67), 10 pages (2016).
"Chapter III Immune Molecules," cited in Office Action in related Chinese Patent Application No. 201180056725.7, 9 pages.
Database Geneseq (online), "Human preproinsulin (PPI) antigenic peptide, Seq ID 164," XP002770300, Jan. 26, 2017, retrieved from EBI accession No. GSP:BDK51134, Database accession No. BDK51134 sequence.
Hemmer, B., et al., "Minimal peptide length requirements for CD4$^+$ T cell clones—implications for molecular mimicry and T cell survival," International Immunology 12(3):375-383 (2000).
Lovitch, S. B., et al., "Amino-Terminal Flanking Residues Determine the Conformation of a Peptide—Class II MHC Complex," The Journal of Immunology 176:2958-2968 (2006).
Pillai, A. B., et al., "Host NKT Cells Can Prevent Graft-versus-Host Disease and Permit Graft Antitumor Activity after Bone Marrow Transplantation," The Journal of Immunology 178:6242-6251 (2007).
Vignali, D. A. A. and Strominger, J. L., "Amino Acid Residues that Flank Core Peptide Epitopes and the Extracellular Domains of CD4 Modulate Differential Signaling through the T Cell Receptor," J Exp Med 179:1945-1956 (1994).
Office Action dated Dec. 1, 2017 in U.S. Appl. No. 14/980,932, filed Dec. 28, 2015, related application.
Office Action dated Sep. 11, 2018 in U.S. Appl. No. 14/980,932, filed Dec. 28, 2015, related application.
Final Office Action dated Jan. 8, 2019 in U.S. Appl. No. 14/980,932, filed Dec. 28, 2015, related application.
Notice of Allowance dated Apr. 3, 2019 in U.S. Appl. No. 14/980,932, filed Dec. 28, 2015, related application.
Office Action dated Oct. 2, 2018 in U.S. Appl. No. 15/388,398, filed Dec. 22, 2016, related application.
Final Office Action dated Apr. 15, 2019 in U.S. Appl. No. 15/388,398, filed Dec. 22, 2016, related application.
Office Action dated Aug. 17, 2016 in U.S. Appl. No. 14/589,134, filed Jan. 5, 2015, related application.
Final Office Action dated Dec. 2, 2016 in U.S. Appl. No. 14/589,134, filed Jan. 5, 2015, related application.
Advisory Action dated Mar. 20, 2017 in U.S. Appl. No. 14/589,134, filed Jan. 5, 2015, related application.
Office Action dated Jul. 14, 2017 in U.S. Appl. No. 14/589,134, filed Jan. 5, 2015, related application.
Final Office Action dated Jan. 19, 2018 in U.S. Appl. No. 14/589,134, filed Jan. 5, 2015, related application.
Office Action dated Oct. 5, 2018 in U.S. Appl. No. 14/589,134, filed Jan. 5, 2015, related application.
Notice of Allowance dated Feb. 21, 2019 in U.S. Appl. No. 14/589,134, filed Jan. 5, 2015, related application.
Office Action dated Aug. 24, 2017 in U.S. Appl. No. 14/450,722, filed Aug. 4, 2014, related application.
Final Office Action dated Dec. 28, 2017 in U.S. Appl. No. 14/450,722, filed Aug. 4, 2014, related application.
Advisory Action dated May 9, 2018 in U.S. Appl. No. 14/450,722, filed Aug. 4, 2014, related application.
Office Action dated Jan. 14, 2019 in U.S. Appl. No. 14/450,722, filed Aug. 4, 2014, related application.
Final Office Action dated Jun. 6, 2019 in U.S. Appl. No. 14/450,722, filed Aug. 4, 2014, related application.

(56) References Cited

OTHER PUBLICATIONS

Office Action dated Sep. 7, 2018 in U.S. Appl. No. 14/894,221, 371(c) date Nov. 25, 2015, related application.
Notice of Allowance dated Apr. 15, 2019 in U.S. Appl. No. 14/894,221, 371(c) date Nov. 25, 2015, related application.
Office Action dated Feb. 23, 2017 in U.S. Appl. No. 14/375,324, 371(c) dated Jul. 29, 2014, related application.
Final Office Action dated Oct. 30, 2017 in U.S. Appl. No. 14/375,324, 371(c) dated Jul. 29, 2014, related application.
Office Action dated Jun. 25, 2018 in U.S. Appl. No. 14/375,324, 371(c) dated Jul. 29, 2014, related application.
Final Office Action dated Mar. 25, 2019 in U.S. Appl. No. 14/375,324, 371(c) dated Jul. 29, 2014, related application.
Office Action dated Feb. 20, 2018 in U.S. Appl. No. 14/976,259, filed Dec. 21, 2015, related application.
Final Office Action dated Oct. 26, 2018 in U.S. Appl. No. 14/976,259, filed Dec. 21, 2015, related application.
Advisory Action dated Feb. 4, 2019 in U.S. Appl. No. 14/976,259, filed Dec. 21, 2015, related application.
Office Action dated May 17, 2019 in U.S. Appl. No. 14/976,259, filed Dec. 21, 2015, related application.
Office Action dated Sep. 18, 2018 in U.S. Appl. No. 15/516,045, 371(c) date Mar. 31, 2017, related application.
Final Office Action dated Feb. 13, 2019 in U.S. Appl. No. 15/516,045, 371(c) date Mar. 31, 2017, related application.
Office Action dated Jan. 20, 2012 in U.S. Appl. No. 12/377,048, 371(c) date Feb. 20, 2009, related application.
Final Office Action dated Aug. 9, 2012 in U.S. Appl. No. 12/377,048, 371(c) date Feb. 20, 2009, related application.
Office Action dated Apr. 20, 2015 in U.S. Appl. No. 12/377,048, 371(c) date Feb. 20, 2009, related application.
Notice of Allowance dated Sep. 22, 2015 in U.S. Appl. No. 12/377,048, 371(c) date Feb. 20, 2009, related application.
Office Action dated Jan. 9, 2014 in U.S. Appl. No. 12/735,744, 371(c) date Aug. 13, 2010, related application.
Final Office Action dated May 20, 2014 in U.S. Appl. No. 12/735,744, 371(c) date Aug. 13, 2010, related application.
Office Action dated Nov. 25, 2014 in U.S. Appl. No. 12/735,744, 371(c) date Aug. 13, 2010, related application.
Final Office Action dated Jun. 5, 2015 in U.S. Appl. No. 12/735,744, 371(c) date Aug. 13, 2010, related application.
Notice of Allowance dated Sep. 28, 2015 in U.S. Appl. No. 12/735,744, 371(c) date Aug. 13, 2010, related application.
Office Action dated Jul. 11, 2013 in U.S. Appl. No. 12/735,739, 371(c) date Aug. 13, 2010, related application.
Final Office Action dated Feb. 20, 2014 in U.S. Appl. No. 12/735,739, 371(c) date Aug. 13, 2010, related application.
Office Action dated Jan. 11, 2016 in U.S. Appl. No. 12/735,739, 371(c) date Aug. 13, 2010, related application.
Final Office Action dated Aug. 11, 2016 in U.S. Appl. No. 12/735,739, 371(c) date Aug. 13, 2010, related application.
Office Action dated Jan. 22, 2013 in U.S. Appl. No. 12/735,740, 371(c) date Aug. 13, 2010, related application.
Final Office Action dated Jul. 10, 2013 in U.S. Appl. No. 12/735,740, 371(c) date Aug. 13, 2010, related application.
Office Action dated Apr. 1, 2014 in U.S. Appl. No. 12/735,740, 371(c) date Aug. 13, 2010, related application.
Notice of Allowance dated Oct. 2, 2014 in U.S. Appl. No. 12/735,740, 371(c) date Aug. 13, 2010, related application.
Notice of Allowance dated Mar. 3, 2015 in U.S. Appl. No. 12/735,740, 371(c) date Aug. 13, 2010, related application.
Office Action dated Jan. 1, 2013 in U.S. Appl. No. 12/735,742, 371(c) date Aug. 13, 2010, related application.
Office Action dated Jun. 17, 2016 in U.S. Appl. No. 13/988,925, 371(c) date Jun. 6, 2013, related application.
Final Office Action dated Dec. 26, 2016 in U.S. Appl. No. 13/988,925, 371(c) date Jun. 6, 2013, related application.
Office Action dated Nov. 9, 2017 in U.S. Appl. No. 13/988,925, 371(c) date Jun. 6, 2013, related application.
Notice of Allowance dated Mar. 26, 2018 in U.S. Appl. No. 13/988,925, 371(c) date Jun. 6, 2013, related application.
Advisory Action dated Apr. 9, 2013, in U.S. Appl. No. 12/735,754, Saint-Remy, J.M., filed Aug. 13, 2010, 3 Pages.
Advisory Action dated Jul. 3, 2017, in U.S. Appl. No. 14/686,855, Saint-Remy, J.M., filed Apr. 15, 2015, 3 Pages.
Advisory Action dated Jun. 27, 2014, in U.S. Appl. No. 12/735,739, Saint-Remy, J.M., filed Aug. 13, 2010, 3 pages.
Advisory Action dated Oct. 22, 2013, in U.S. Appl. No. 12/735,740, Saint-Remy, J.M., filed Aug. 13, 2010, 3 pages.
Advisory Action dated Oct. 3, 2019, in U.S. Appl. No. 14/450,722, Saint-Remy, J.M., filed Aug. 4, 2014, 3 pages.
Advisory Action dated Sep. 9, 2019, in U.S. Appl. No. 15/388,398, Saint-Remy, J.M., filed Dec. 22, 2016, 12 Pages.
Ali-Khan, N., et al., "Overview of Proteome Analysis," Current Protocols in Protein Science, 30(1):22.1.1-22.1.19, Hoboken, NJ : Wiley Interscience, United States (Dec. 2002).
Celis, E., et al., "Identification of Potential CTL Epitopes of Tumor-associated Antigen MAGE-1 for Five Common HLA-A Alleles," Molecular Immunology, 31(18):1423-1430, Pergamon Press, England (Dec. 1994).
Co-pending U.S. Appl. No. 16/507,133, filed Jul. 10, 2019.
DermNet NZ, 2019.
Final Office Action dated Nov. 5, 2019, in U.S. Appl. No. 14/450,722, Saint-Remy, J.M., filed Aug. 4, 2014, 8 Pages.
Final Office Action dated Aug. 7, 2019, in U.S. Appl. No. 15/516,045, Saint-Remy, J.M., et al., filed Mar. 31, 2017, 5 pages.
Final Office Action dated Mar. 23, 2017, in U.S. Appl. No. 14/686,855, Saint-Remy, J.M., filed Apr. 15, 2015, 11 Pages.
Final Office Action dated Sep. 26, 2012, in U.S. Appl. No. 12/735,754, Saint-Remy, J.M., filed Aug. 13, 2010, 18 Pages.
Fournier, P. and Schirrrnacher, V., "Randomized Clinical Studies of Anti-tumor Vaccination: State of the Art in 2008," Expert Review of Vaccines, 8(1):51-66, Taylor & Francis, England (Jan. 2009).
Heurtault, B., et al., "Design of a Liposomal Candidate Vaccine Against *Pseudomonas aeruginosa* and Its Evaluation in Triggering Systemic and Lung Mucosal Immunity," Pharmaceutical Research, 26(2):276-285, Kluwer Academic/Plenum Publishers, United States (Feb. 2009).
HLA Nomenclature, 2015.
International Search Report and Written Opinion for International Application No. PCT/EP2015/074063, European Patent Office, Netherlands, dated Jan. 29, 2016, 8 Pages.
International Search Report and Written Opinion for International Application No. PCT/EP2017/059302, European Patent Office, Netherlands, dated Jun. 26, 2017, 11 Pages.
International Search Report and Written Opinion for International Application No. PCT/EP2018/055501, European Patent Office, Netherlands, dated May 4, 2018, 13 Pages.
International Search Report for International Application No. PCT/BE2008/000010, European Patent Office, Germany, dated Jul. 2, 2008.
International Search Report for International Application No. PCT/BE2013/000006, European Patent Office, Netherlands, dated Jul. 1, 2013, 8 Pages.
International Search Report for International Application No. PCT/EP2007/007165, European Patent Office, Netherlands, dated Jan. 17, 2008.
International Search Report for International Application No. PCT/EP2009/051803, European Patent Office, Netherlands, dated Aug. 11, 2009, 5 Pages.
International Search Report for International Application No. PCT/EP2009/051804, European Patent Office, Netherlands, dated Aug. 11, 2009, 6 Pages.
International Search Report for International Application No. PCT/EP2009/051806, European Patent Office, Netherlands, dated Aug. 11, 2009, 6 Pages.
International Search Report for International Application No. PCT/EP2009/051807, European Patent Office, Netherlands, dated Jul. 13, 2009, 5 Pages.
International Search Report for International Application No. PCT/EP2009/051808, European Patent Office, Netherlands, dated Feb. 18, 2010, 7 Pages.

(56) References Cited

OTHER PUBLICATIONS

International Search Report for International Application No. PCT/EP2014/060994, European Patent Office, Netherlands, dated Sep. 18, 2014, 5 pages.
Lamb, J.R., et al., "Human T-Cell Clones Recognize Chemically Synthesized Peptides of Influenza Haemagglutinin," Nature, 300:66-69, Springer, United States (Nov. 1982).
Non-Final Office Action dated Jan. 20, 2012, in U.S. Appl. No. 12/735,754, Saint-Remy, J.M., filed Aug. 13, 2010, 16 Pages.
Non-Final Office Action dated Jul. 24, 2014, in U.S. Appl. No. 12/735,754, Saint-Remy, J.M., filed Aug. 13, 2010, 13 Pages.
Non-Final Office Action dated Oct. 2, 2019, in U.S. Appl. No. 14/375,324, Saint-Remy, J.M., filed Jul. 29, 2014, 10 Pages.
Notice of Allowance dated Dec. 2, 2019, in U.S. Appl. No. 14/980,932, Saint-Remy, J.M., filed Dec. 28, 2015, 7 pages.
Notice of Allowance dated Jan. 30, 2015, in U.S. Appl. No. 12/735,754, Saint-Remy, J.M., filed Aug. 13, 2010, 9 Pages.
Notice of Allowance dated Nov. 26, 2019, in U.S. Appl. No. 14/589,134, Saint-Remy, J.M., filed Jan. 5, 2015, 9 Pages.
Notice of Allowance dated Sep. 27, 2019, in U.S. Appl. No. 15/388,398, Saint-Remy, J.M., filed Dec. 22, 2016, 11 Pages.
Notice of Allowance dated Sep. 7, 2017, in U.S. Appl. No. 14/686,855, Saint-Remy, J.M., filed Apr. 15, 2015, 11 Pages.
Schwartz, R.H., et al., "The T Lymphocyte Response to Cytochrome c. V. Determination of the Minimal Peptide Size Required for Stimulation of T Cell Clones and Assessment of the Contribution of Each Residue Beyond This Size to Antigenic Potency," Journal of Immunology, 135(4):2598-2608, American Association of Immunologists, United States (Oct. 1985).
ViralZone, 2017.
Witmer, C. and Young, G., "Factor VIII Inhibitors in Hemophilia a: Rationale and Latest Evidence," Therapeutic Advances in Hematology, 4(1):59-72, Sage, England (Feb. 2013).

Written Opinion for International Application No. PCT/EP2007/007165, European Patent Office, Netherlands, dated Jan. 17, 2008, 8 Pages.
Written Opinion for International Application No. PCT/EP2009/051803, European Patent Office, Netherlands, dated Aug. 11, 2009, 7 Pages.
Written Opinion for International Application No. PCT/EP2009/051804, European Patent Office, Netherlands, dated Aug. 11, 2009, 8 Pages.
Written Opinion for International Application No. PCT/EP2009/051807, European Patent Office, Netherlands, dated Jul. 13, 2009, 5 Pages.
Written Opinion for International Application No. PCT/EP2009/051808, European Patent Office, Netherlands, dated Feb. 18, 2010, 7 Pages.
Written Opinion for International Application No. PCT/EP2014/060994, European Patent Office, Netherlands, dated Jun. 1, 2015, 7 pages.
Written Opinion for International Application No. PCT/EP2014/060994, European Patent Office, Netherlands, dated Sep. 18, 2014, 6 pages.
Written Opinion of the International Preliminary Examining Authority for International Application No. PCT/BE2013/000006, European Patent Office, Germany, dated Feb. 14, 2014, 15 Pages.
Written Opinion of the International Searching Authority for International Application No. PCT/BE2008/000010, European Patent Office, Germany, dated Jul. 2, 2008, 8 Pages.
Written Opinion of the International Searching Authority for International Application No. PCT/BE2013/000006, European Patent Office, Germany, dated Jul. 1, 2013, 10 Pages.
Written Opinion of the International Searching Authority for International Application No. PCT/EP2009/051806, European Patent Office, Netherlands, dated Aug. 11, 2009, 7 Pages.

* cited by examiner

SEQUENCE LISTING

```
<160> NUMBER OF SEQ ID NOS: 12

<210> SEQ ID NO 1
<211> LENGTH: 13
<212> TYPE: PRT
<213> ORGANISM: Artificial Sequence
<220> FEATURE:
<223> OTHER INFORMATION: membrane cofactor protein (MCP) fragment

<400> SEQUENCE: 1

Pro Tyr Arg Tyr Leu Gln Arg Arg Lys Lys Lys Gly Lys
1               5                   10

<210> SEQ ID NO 2
<211> LENGTH: 18
<212> TYPE: PRT
<213> ORGANISM: Artificial Sequence
<220> FEATURE:
<223> OTHER INFORMATION: redox motif + MCP fragment

<400> SEQUENCE: 2

Cys Pro Tyr Cys Val Pro Tyr Arg Tyr Leu Gln Arg Arg Lys Lys Lys
1               5                   10                  15

Gly Lys

<210> SEQ ID NO 3
<211> LENGTH: 18
<212> TYPE: PRT
<213> ORGANISM: Artificial Sequence
<220> FEATURE:
<223> OTHER INFORMATION: redox motif + human Factor VIII fragment

<400> SEQUENCE: 3

Cys Gly His Cys Gly Gly Phe Thr Asn Met Phe Ala Thr Trp Ser Pro
1               5                   10                  15
```

Ser Lys

<210> SEQ ID NO 4
<211> LENGTH: 17
<212> TYPE: PRT
<213> ORGANISM: Artificial Sequence
<220> FEATURE:
<223> OTHER INFORMATION: redox motif + human factor VIII fragment

<400> SEQUENCE: 4

Cys Pro Tyr Cys Val Pro Gln Thr Leu His Lys Phe Ile Leu Leu Phe
1               5                   10                  15

Ala

<210> SEQ ID NO 5
<211> LENGTH: 12
<212> TYPE: PRT
<213> ORGANISM: Artificial Sequence
<220> FEATURE:
<223> OTHER INFORMATION: human Factor VIII fragment

<400> SEQUENCE: 5

Cys Gln Thr Leu His Lys Phe Ile Leu Leu Phe Ala
1               5                   10

<210> SEQ ID NO 6
<211> LENGTH: 8
<212> TYPE: PRT
<213> ORGANISM: Artificial Sequence
<220> FEATURE:
<223> OTHER INFORMATION: fragment of anti-TNF alpha antibody

<400> SEQUENCE: 6

Tyr Tyr Ala Pro Trp Cys Asn Asn
1               5

<210> SEQ ID NO 7
<211> LENGTH: 14
<212> TYPE: PRT
<213> ORGANISM: Artificial Sequence
<220> FEATURE:
<223> OTHER INFORMATION: redox motif + fragment of anti TNF alpha
      antibody

<400> SEQUENCE: 7

Cys Pro Tyr Cys Val Pro Tyr Tyr Ala Pro Trp Cys Asn Asn
1               5                   10

<210> SEQ ID NO 8
<211> LENGTH: 4
<212> TYPE: PRT
<213> ORGANISM: artificial sequence
<220> FEATURE:
<223> OTHER INFORMATION: redox motif
<220> FEATURE:
<221> NAME/KEY: variant
<222> LOCATION: (1)..(1)
<223> OTHER INFORMATION: Xaa is Cys, Ser or Thr
<220> FEATURE:
<221> NAME/KEY: variant
<222> LOCATION: (2)..(2)
<223> OTHER INFORMATION: Xaa can be any amino acid
<220> FEATURE:
<221> NAME/KEY: variant
<222> LOCATION: (3)..(3)
<223> OTHER INFORMATION: Xaa can be any amino acid

<400> SEQUENCE: 8

Xaa Xaa Xaa Cys
1

<210> SEQ ID NO 9
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc_feature
<222> LOCATION: (2)..(2)
<223> OTHER INFORMATION: Xaa can be any amino acid sequence
<220> FEATURE:
<221> NAME/KEY: misc_feature
<222> LOCATION: (3)..(3)
<223> OTHER INFORMATION: Xaa can be any amino acid sequence
<220> FEATURE:
<221> NAME/KEY: misc_feature
<222> LOCATION: (4)..(4)
<223> OTHER INFORMATION: Xaa is Cys, Ser or Thr

<400> SEQUENCE: 9

Cys Xaa Xaa Xaa
1

<210> SEQ ID NO 10
<211> LENGTH: 4
<212> TYPE: PRT
<213> ORGANISM: artificial sequence
<220> FEATURE:
<223> OTHER INFORMATION: redox motif
<220> FEATURE:
<221> NAME/KEY: VARIANT
<222> LOCATION: (2)..(2)
<223> OTHER INFORMATION: Xaa can be any amino acid
<220> FEATURE:
<221> NAME/KEY: VARIANT
<222> LOCATION: (3)..(3)
<223> OTHER INFORMATION: Xaa can be any amino acid

<400> SEQUENCE: 10

Cys Xaa Xaa Cys
1

<210> SEQ ID NO 11
<211> LENGTH: 7
<212> TYPE: PRT
<213> ORGANISM: Artificial Sequence
<220> FEATURE:
<223> OTHER INFORMATION: NKT motif
<220> FEATURE:
<221> NAME/KEY: variant
<222> LOCATION: (1)..(1)
<223> OTHER INFORMATION: Xaa is Phe, Trp, Thr, His or Tyr
<220> FEATURE:
<221> NAME/KEY: variant
<222> LOCATION: (2)..(2)
<223> OTHER INFORMATION: Xaa can be any amino acid
<220> FEATURE:
<221> NAME/KEY: variant
<222> LOCATION: (3)..(3)
<223> OTHER INFORMATION: Xaa can be any amino acid
<220> FEATURE:
<221> NAME/KEY: variant
<222> LOCATION: (4)..(4)
<223> OTHER INFORMATION: Xaa is Val, Ile, Leu or Met
<220> FEATURE:
<221> NAME/KEY: variant
<222> LOCATION: (5)..(5)
<223> OTHER INFORMATION: Xaa can be any amino acid
<220> FEATURE:
<221> NAME/KEY: variant
<222> LOCATION: (6)..(6)

```
<223> OTHER INFORMATION: Xaa can be any amino acid
<220> FEATURE:
<221> NAME/KEY: variant
<222> LOCATION: (7)..(7)
<223> OTHER INFORMATION: Xaa is Phe, Trp, Thr, His or Tyr

<400> SEQUENCE: 11

Xaa Xaa Xaa Xaa Xaa Xaa Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: NKT motif
<220> FEATURE:
<221> NAME/KEY: variant
<222> LOCATION: (1)..(1)
<223> OTHER INFORMATION: Xaa is Phe, Trp, His  or Tyr
<220> FEATURE:
<221> NAME/KEY: variant
<222> LOCATION: (2)..(2)
<223> OTHER INFORMATION: Xaa can be any amino acid
<220> FEATURE:
<221> NAME/KEY: variant
<222> LOCATION: (3)..(3)
<223> OTHER INFORMATION: Xaa can be any amino acid
<220> FEATURE:
<221> NAME/KEY: variant
<222> LOCATION: (4)..(4)
<223> OTHER INFORMATION: Xaa is Val, Ile,  Leu  or  Met
<220> FEATURE:
<221> NAME/KEY: variant
<222> LOCATION: (5)..(5)
<223> OTHER INFORMATION: Xaa can be any amino acid
<220> FEATURE:
<221> NAME/KEY: variant
<222> LOCATION: (6)..(6)
<223> OTHER INFORMATION: Xaa can be any amino acid
<220> FEATURE:
<221> NAME/KEY: variant
<222> LOCATION: (7)..(7)
<223> OTHER INFORMATION: Xaa is Phe, Trp, His  or Tyr

<400> SEQUENCE: 12

Xaa Xaa Xaa Xaa Xaa Xaa Xaa
1               5
```

ANIMAL MODELS FOR EVALUATING PHARMACEUTICAL COMPOUNDS

This application claims priority to EP Patent Application No. 15167964.4 filed May 18, 2015, the entire contents of which is hereby incorporated by reference.

FIELD OF THE INVENTION

The present invention relates to methods by which animals can be rendered unresponsive to single pharmaceutical compounds with antigenic properties which can be assessed in these animal models for pharmacokinetic properties and toxicity. The invention further relates to the use of such animals to assess pharmacokinetic properties and toxicity of pharmaceutical compounds. The invention also relates to animals rendered specifically unresponsive to these pharmaceutical compounds.

BACKGROUND OF THE INVENTION

Thousands of pharmaceutical compounds are tested every year for pharmacokinetic properties and potential toxicity prior to clinical use. A major part of these tests is performed by administering a pharmaceutical compound to an animal and by assessing pharmacokinetic properties and/or toxicity at various points in time. These studies are, however, severely limited by the fact that the vast majority of pharmaceutical compounds elicit an immune response. Such an immune response is usually rapid, occurring within days or weeks, thereby drastically reducing the period of time during which an animal can be observed for evaluating pharmacokinetic properties and possible toxicity of pharmaceutical compounds. Obviously, the immune response also precludes any re-administration of pharmaceutical compounds.

The nature of an immune response can vary, from the elicitation of antibodies to the development of a cellular response, depending on the physicochemical properties of the antigen, the genetic background of the animal, the route, the doses and the frequency of administration. However, such immune response depends on antigen recognition by lymphocytes and activation of these cells, which belong to the CD4+ subset. Once activated, CD4+ T cells dictate the form and the fate of the response at multiple levels, including, yet not limited, activation of innate immunity, activation of B cells to mature and produce specific antibodies, enhancement of the capacity of antigen-presenting cells to activate CD8+ T cells, recruitment and activation of naïve CD4+ T cells and activation of cell immunity such as delayed type response, as observed with chemicals.

Considering the central role of CD4+ T cells in all these processes, a method by which it would become feasible to specifically prevent and/or suppress their activation would provide a highly specific state of immune tolerance to the pharmaceutical compound under evaluation (protein or non-protein organic compound).

Patent application WO2008017517 describes class II-restricted epitopes to which an oxidoreductase motif is added within residues flanking the amino acid sequence which fits into the class II major histocompatibility complex (MHC) cleft. Inclusion of an oxidoreductase motif converts an effector CD4+ T cell into a potent cytolytic cell, inducing apoptosis of the antigen-presenting cell with which a synapse has been formed, thereby preventing activation of effector cells of adaptive immunity. This concept is further elaborated for soluble allofactors (WO2009101206), intracellular pathogens (WO2009101208) and tumor associated antigens (WO2009101205).

WO2012069568 patent application describes CD1d-restricted T cell peptide epitopes to which an oxidoreductase motif is added within residues of the flanking sequence. Such peptide converts NKT cells into strong cytolytic cells eliminating the antigen-presenting cell with which a synapse is formed, thereby preventing activation of effector cells of innate immunity.

The above publications describe methods of prevention wherein healthy animals are treated with a peptide with redox motif and epitope of a pathogen, allergen, or autoantigen and are subsequently challenged with the disease causing agent.

The above publications describe methods of treatment wherein diseased animals (or models for such disease) are treated with a peptide with redox motif and an epitope of a therapeutic protein to prevent a subsequent immune response to this therapeutic protein.

SUMMARY OF THE INVENTION

As a common general concept of the present invention, pharmaceutical compounds for diseases or disorders are being tested in model organisms wherein the pharmaceutical compound has no medicinal effect, because the compound is administered to a healthy animal, i.e. an animal without symptoms or signs, or not suffering from the disease for which the pharmaceutical is intended.

The models of the present invention differ from the above described prior art in that healthy animals are made tolerant against a pharmaceutical compound, and that subsequently the pharmaceutical compound is administered to this healthy animal.

The present invention therefore relates to methods to obtain antigen-specific tolerant animals, the animals and their use for evaluating the pharmacokinetic properties and toxicity of pharmaceutical compounds.

The present invention has the advantage that the period of time during which an animal can be observed for evaluating pharmacokinetic properties and possible toxicity of pharmaceutical compounds, will be for a much longer period than the usual few days of weeks wherein in normal animals an immune response occurs.

The present invention provides the further advantage that re-administration of pharmaceutical compounds can be performed in test animals.

The methods of the present invention have the advantage that the immune response to one compound is eliminated in an animal without affecting the overall immune reactivity.

The present invention further extends to animals directly obtained by the methods of the present invention.

One aspect of the present invention relates to methods for determining a parameter of a pharmaceutical compound against a disease or disorder. These methods comprise the steps of:

providing a non-human animal which is not suffering from or is not showing symptoms or signs of this disorder and which does not provoke an immune response against this pharmaceutical compound, whereby the animal is obtainable by administration of a peptide comprising an oxidoreductase motif with the sequence [CTS]-x-x-C [SEQ ID NO: 8] or [C]-x-x-[CST] [SEQ ID NO: 9] and further comprising an NKT peptide epitope or an MHC class II T cell epitope of this pharmaceutical compound, wherein the motif and the epitope are separated by a linker of between 0 and 4 amino acids, administering the pharmaceutical compound to the non-human animal, measuring a parameter of the pharmaceutical compound in the non-human animal.

In embodiments hereof the pharmaceutical compound is a protein and the epitope sequence is a fragment of this protein.

In more specific embodiments, the pharmaceutical compound is a protein with a conformation dependent epitope and the epitope sequence is a mimotope of this conformation dependent epitope.

In other embodiments the pharmaceutical compound is not proteic and the epitope sequence is the sequence of a mimotope for said pharmaceutical compound.

In specific embodiments of the methods the motif is C-x-x-C [SEQ ID NO: 10].

In specific embodiments of the methods the NKT peptide epitope has the motif [FWTHY]-$X_2X_3$-[ILMV]-$X_5X_6$-[FWTHY] [SEQ ID NO: 11].

In specific embodiments of the methods the animal is not a primate, for example a rodent.

In specific embodiments of the methods the animal is an outbred animal.

In embodiments of these methods the parameter is selected from one or more of the group consisting of toxicity, half life time, body weight, mobility, feeding habits, breathing, water and motion passing, aspect of the fur, etc.

Another aspect of the invention related to non-therapeutic methods for rendering a non-human animal non-responding to an immune response against a pharmaceutical compound against a disease or disorder comprising the steps of:

providing a non-human animal which is not suffering from or is not showing symptoms or signs of this disease or disorder, and which has not received this pharmaceutical compound, administering a peptide comprising:

an oxidoreductase motif with the sequence [CTS]-x-x-C [SEQ ID NO: 8] or [C]-x-x-[CST] [SEQ ID NO: 9], and a NKT peptide epitope or an MCH class II T cell epitope of this pharmaceutical compound, wherein motif and epitope are separated by linker of between 0 and 4 amino acids.

Another aspect relates to non-human animals, which are non-responding to an immune response against a pharmaceutical compound against a disease or disorder, obtainable by the above methods.

Another aspect relates to use of such non-human animal in toxicity testing of a pharmaceutical, or in determining a pharmacokinetic parameter of a pharmaceutical.

Definitions

"Pharmaceutical compounds" in the context of the present invention refers to any compound with demonstrated or expected beneficial medical activity that can provoke an immune response. Examples hereof are peptides and proteins, as well as small chemicals. Such small chemicals bind to host animal proteins such as albumin and can act as an hapten in triggering an immune response.

"healthy animal" refers to wild type animals or inbred laboratory strains, and this in relation to the pharmaceutical compound which is tested in the methods of the present invention.

The healthy status of the animal with respect to the pharmaceutical compound under investigation for a disease or disorder implies that the animal has not the discomfort caused by this disease and does not show the symptoms or signs caused by this disease or disorder.

Thus animals may have disorders or diseases other than the one which is being treated by the pharmaceutical compound under investigation.

When the animal is a transgenic animal, the transgene is unrelated related to the pathology which is treated by the pharmaceutical compound.

Thus for example, an anticoagulant is not tested in an animal with inflicted wounds or wherein coagulation inhibitors are administered. Similarly an anticoagulant is not tested in an animal with a transgene (esp. knock-out) for a component of the coagulation pathway.

The term "peptide or protein" when used herein refers to a molecule comprising an amino acid sequence of at least 2 amino acids, connected by peptide bonds, but which can in a particular embodiment comprise non-amino acid structures (like for example a linking organic compound). Peptides according to the invention can contain any of the conventional 20 amino acids or modified versions thereof, or can contain non-naturally occurring amino acids incorporated by chemical peptide synthesis or by chemical or enzymatic modification, as well as modified amino and/or carboxyterminus.

The difference between peptides and protein is mainly arbitrarily made in the art whereby peptides are typically smaller than 50 amino acids and proteins larger than 50 amino acids.

In the context of the present invention, the combination of the redox motif and an or more epitopes in a polypeptide will be referred to as "peptide" although the length can range from 12, up to 20, 25, 30, 40, 50, 75 or up to 100 amino acids.

Pharmaceutical compounds with peptide bonds can be as small as 4 -10 amino acids for certain peptide hormones (often with posttranslational modifications) at the one end, up to large protein complexes of more than 100 amino acids such as therapeutic antibodies at the other hand.

"Pharmacokinetic parameter" in the present invention relates to properties such as half-life time, uptake into specific cell types or tissues, metabolism into other compounds. Other parameters which can be tested are behavioral, physical and clinical parameters such as body weight, mobility, feeding habits, breathing, water and motion passing, aspect of the fur.

The term "epitope" when used herein refers to one or several portions (which may define a conformational epitope) of a protein which is/are specifically recognized and bound by an antibody or a portion thereof (Fab', Fab2', etc.) or a receptor presented at the cell surface of a B or T cell lymphocyte, and which is able, by this binding, to induce an immune response.

The term "antigen" when used herein refers to a structure of a macromolecule comprising one or more hapten(s) and/or comprising one or more T cell epitopes. Typically, this macromolecule is a protein or peptide (with or without polysaccharides) and comprises one or more epitopes; such macromolecule can herein alternatively be referred to as "antigenic protein" or "antigenic peptide".

The term "hapten" when used herein refers to a small molecule which can only induce an immune response when bound to a carrier protein, either exogenous or endogenous.

The term "immunogen" when used herein refers to a molecule which can stimulate a cellular or humoral immune response The term "T cell epitope" or "T-cell epitope" in the context of the present invention refers to a dominant, sub-dominant or minor T cell epitope, i.e., a part of an antigenic protein that is specifically recognized and bound by a receptor at the cell surface of a T lymphocyte. Whether an epitope is dominant, sub-dominant or minor depends on the immune reaction elicited against the epitope. Dominance depends on the frequency at which such epitopes are recognized by T cells and able to activate them, among all the possible T cell epitopes of a protein. In particular, a T cell epitope is an epitope bound by MHC class I or MHC class II molecules.

The term "NKT cell peptide epitope" refers to a part of an antigenic protein that is specifically recognized and bound by a receptor at the cell surface of a T lymphocyte. In particular, a NKT cell peptide epitope is an epitope bound by CD1d molecules, with motif [FWTHY]-$X_2X_3$-[ILMV]-$X_5X_6$-[FWTHY] [SEQ ID NO:11] or a more restrictive form thereof as explained further below.

The term "CD4+ effector cells" refers to cells belonging to the CD4-positive subset of T-cells whose function is to provide help to other cells, such as, for example B-cells. These effector cells are conventionally reported as Th cells (for T helper cells), with different subsets such as Th0, Th1, Th2, and Th17 cells.

The term "NKT cells" refers to cells of the innate immune system characterized by the fact that they carry receptors such as NK1.1 and NKG2D, and recognize peptide epitopes presented by the CD1d molecule. In the context of the present invention, NKT cells can belong to either the type 1 (invariant) or the type 2 subset, or to any of the less characterized NKT cells with more polymorphic T cell receptors than type 1 or type 2 NKT cells.

The "CD1d molecule" refers to a non-MHC derived molecule made of 3 alpha chains and an anti-parallel set of beta chains arranged into a deep hydrophobic groove opened on both sides and capable of presenting lipids, glycolipids or hydrophobic peptides to NKT cells.

The term "immune disorders" or "immune diseases" refers to diseases wherein a reaction of the immune system is responsible for or sustains a malfunction or non-physiological situation in an organism. Immune disorders in the context of the present invention refer to pathology induced by infectious agents and tumor surveillance.

The term "allofactor" refers to a protein, peptide or factor (i.e. any molecule) displaying polymorphism when compared between two individuals of the same species, and, more in general, any protein, peptide or factor that induces an (alloreactive) immune response in the subject receiving the allofactor.

The term "alloantigen" or "allograft antigen" when used herein refer to an antigen derived from (shed from and/or present in) a cell or tissue which, when transferred from a donor to a recipient, can be recognized and bound by an antibody of B or T-cell receptor of the recipient. Alloantigens are typically products of polymorphic genes. An alloantigen is a protein or peptide which, when compared between donor and recipient (belonging to the same species), displays slight structural differences. The presence of such a donor antigen in the body of a recipient can elicit an immune response in the recipient. Such alloreactive immune response is specific for the alloantigen.

The term "thiol-oxidoreductase motif", "oxido-reductase", "thioreductase motif", "thioredox motif" or "redox motif" are used here as synonymous terms and refers to the sequence motif C-X-X-[CST] [SEQ ID NO: 9] or [CST]-X-X-C [SEQ ID NO: 8], in which C stands for cysteine, S for serine, T for threonine and X for any amino acid.

DETAILED DESCRIPTION

Thousands of new molecules are considered for use in therapy and as such are tested for efficacy, pharmacokinetic properties and for potential toxicity in animal models. Rodents, including mice, rats and guinea-pigs are the most often used models for their ease of use, availability of syngeneic strains and of evaluation tools. Other animal models include rabbits, pigs, dogs and horses. These animals diverge much from human beings in terms of capacity to mount an immune response against a molecule considered for therapy and very often make an early response which is of no relevance for the pathophysiology of human beings, but precludes an assessment of the efficacy of the molecule, its pharmacokinetic properties, as well as long-term toxicity assessment. This severely restricts the usefulness of such animal models. In order to palliate such difficulties, non-human primates can be used, but the cost related to such experiments very much restricts the number of tested animals, and thereby the strength of the statistical evaluation. Besides, although there is a high homology between human and non-human primate genomes, variations observed between individual animals contribute to the limited value of these study outcomes.

There is therefore an urgent need for improved systems by which a pharmaceutical compound could be tested. Optimally, an animal should be rendered tolerant or unresponsive to the pharmaceutical compound, using a method preventing and/or suppressing its capacity to mount an immune response to this compound without affecting other parts of its immune system. The animal would then be suitable for evaluating pharmacokinetic properties and toxicity of this molecule.

The WO2008017517 patent application describes a method wherein class II-restricted epitopes are used either by direct vaccination or for in vitro conversion of class II-restricted T cells, resulting in acquisition by CD4+ T cells of strong cytolytic properties, inducing apoptosis of the antigen-presenting cell (presenting the protein containing the epitope sequence used to design the peptide) with which a synapse has been formed, thereby preventing activation of effector cells of adaptive immunity.

The WO2012069568 patent application describes a method wherein CD1d-restricted peptide epitopes are used either by direct vaccination or for in vitro conversion of CD1d-restricted NKT cells, resulting in acquisition by NKT cells of strong cytolytic properties, inducing apoptosis of the antigen-presenting cell (presenting the protein containing the epitope sequence used to design the peptide) with which a CD1d synapse has been formed, thereby preventing activation of effector NKT cells.

In both these patent applications, the invention comprises the inclusion of an oxidoreductase motif within residues of the sequence flanking the epitope sequence, which is sufficient to obtain the cytolytic conversion of either class II-restricted T cells or CD1d-restricted NKT cells.

Animals in need of treatment or prevention described in patent application WO2008017517 or WO2012069568 are rendered unresponsive to a therapeutic protein. In fact, by switching off activation of either class II-restricted or CD1d-restricted (NK)T cells, the method prevents all the consequences linked to this activation. These include stimulation of B cells for the production of specific antibodies, activation of cytolytic class I-restricted CD8+ T cells, activation of antigen-presenting cells leading to increased cytokine production and increased expression of MHC determinants.

Pharmaceutical compounds can contain class II-restricted epitopes, CD1d-restricted peptide epitopes, or both types of epitopes. A significant number of proteins contain class II-restricted epitopes but no CD1d-restricted peptide epitopes. This is due to the particular nature of peptides presented by CD1d, which contain hydrophobic residues at key locations.

However, CD1d offers very limited polymorphism, which allows extrapolating conclusions from one animal model to another of the same animal species. This is not feasible for class II determinants, which may necessitate the design of alternative peptides to induce unresponsiveness when using several animal models of the same species.

A sequence fragment of a protein can contain both a class II-restricted epitope as well as a CD1d-restricted peptide epitope. In such a case, and depending on the molecule under testing, a single peptide could result in unresponsiveness of both class II-restricted and CD1d-restricted (NK)T cells.

Identification of epitopes suitable for the present invention are known in the art. Class II-restricted epitopes are obtained by using a combination of in silico algorithms, literature search and in vitro or in vivo testing.

CD1d-restricted peptide epitopes are also identified by algorithms and correspond to a sequence motif made of general sequence [FWTHY]-$X_2X_3$-[ILMV]-$X_5X_6$-[FWTHY] [SEQ ID NO:11]. It should however be clear for those skilled in the art that the motif is symmetrical and that P7 can be considered as P1, and P1 can be considered as P7. The above motif can be more restrictive whereby independently from each other the choice of the amino acid at P1 or P7 can be [FWTH] or [FWHY] or [FWY] or [FW] and the choice of the amino acid at P4 can be [ILM].

Identification of class II-restricted epitopes in proteins is obtained as described in detail in WO2008017517.

The identification and selection of a T-cell epitope in a protein is as follows:

(1) one or more in vitro algorithms can be used to identify a T cell epitope sequence within this protein. Suitable algorithms include, but are not limited to those found on the following websites:

antigen.i2r.a-star.edu.sg/predBalbc/;
imtech.res.in/raghava/mhcbn/;
syfpeithi.de/home.htm;
bs.informatik.uni-tuebingen.de/SVMHC;
bio.dfci.harvard.edu/Tools/antigenic.html;
www.jenner.ac.uk/MHCPred/

These algorithms are described in Zhang et al. (2005) *Nucleic Acids Res* 15, W180-W183 (PREDBALB); Salomon & Flower (2006) *BMC Bioinformatics* 7, 501 (MHCBN); Schuler et al. (2007) *Methods Mol Biol.* 409, 75-93 (SYFPEITHI); Donnes & Kohlbacher (2006) *Nucleic Acids Res.* 34, W194-W197 (SVMHC); Kolaskar & Tongaonkar (1990) *FEBS Lett.* 276, 172-174 and Guan et al. (2003) *Appl Bioinformatics* 2, 63-66 (MHCPred).

More particularly, such algorithms allow the prediction within an antigenic protein of one or more nonapeptide sequences which will fit into the groove of an MHC II molecule.

(2) isolated peptide sequences of this protein are tested by, for example, T cell biology techniques, to determine whether the peptide sequences elicit a T cell response. Those peptide sequences found to elicit a T cell response are defined as having T cell stimulating activity as measured, e.g., by cellular uptake of tritiated thymidine.

(3) class II-restricted T-cell epitopes can further optionally be tested on their binding affinity to MHC class II molecules. This can be performed in different ways. For instance, soluble HLA class II molecules are obtained by lysis of cells homozygous for a given class II molecule. The latter is purified by affinity chromatography. Soluble class II molecules are incubated with a biotin-labelled reference peptide produced according to its strong binding affinity for that class II molecule. Peptides to be assessed for class II binding are then incubated at different concentrations and their capacity to displace the reference peptide from its class II binding is calculated by addition of neutravidin. Methods can be found in for instance Texier et al. (2000) *J. Immunology* 164, 3177-3184.

As an alternative overlapping peptide fragments of a protein can be tested in the above assays.

Identification of CD1d-restricted peptide epitopes in therapeutic proteins is described in detail in WO2012069568.

(1) optionally, evaluation of the capacity to activate NKT cells. This is carried out by incubating this protein with a cell line expressing the CD1d molecule. Examples of such cell lines are known in the art (for instance JAWS2 cells). Efficient presentation of the peptide or polypeptide by the CD1d molecule is then evaluated by measuring the activation of NKT cells, obtained from peripheral blood. These methods are described in the art (e.g. Brutkiewicz (2006) *J. Immunol.* 177, 769-775).

(2) the protein is screened for the presence of at least one motif corresponding to the [FWHY]-$X_2X_3$-[ILMV]-$X_5X_6$-[FWHY] [SEQ ID NO:12] sequence (putative CD1d binding motif) using algorithms well known in the art such as expasy.org/tools/scanprosite/ [Sigrist et al. (2002) *Brief Bioinform.* 3, 265-274]

(3) Optionally, a synthetic peptide encompassing the CD1d binding motif is tested in vitro using a cell line expressing the CD1d molecule as described in (1).

(4) Optionally, the synthetic peptide encompassing the sequence containing a CD1d binding motif is tested in vitro using tetramers of the CD1d molecule to detect NKT cells specific for such peptide.

A hapten is a small molecule which cannot by itself generate an immune response. However, a hapten can become strongly immunogenic when bound to a protein carrier. In most instances, the carrier is albumin, the most abundant protein in circulation. However, hapten can bind to cell surface, thereby generating a full immunogen. One example of this is provided by binding of heparin to the surface of platelets, which can elicit an immune response leading to the production of antibodies with potent platelet lysis potential. Heparin acts as a hapten and platelet factor 4 at the surface of the platelet acts as a carrier.

The present definition of a hapten also comprises specific situations in which the hapten binds directly to a major histocompatibility molecule and thereby generate the possibility of activating T cells directly. Under such circumstances, the MHC molecules allow the presentation to T cells, which is a property similar to that of a carrier-hapten. In further situations, the hapten binds directly to a specific T cell receptor (TCR), allowing the reactivity of the hapten TCR complex to activate itself on MHC molecules. Demonstration of these situations are to be found, for instance, in Weltzien H U, in Drug hypersensitivity, ed. W J Pichler, Karger, 2007; pp 47-54, and in Gerber B O and Pichler W J. *ibid,* pp 66-73. In these two situations, peptides encompassing T cell epitopes (class II-restricted as well as CD1d-restricted) are made of conformational changes of the MHC sequence.

Huang 3 et al. (2002) *Nucl. Acids Res.* 40, D271-D277 describe a database (MimoDB) of peptides which act as mimotopes for a variety of immunogenic compounds.

Methods to reproduce conformational epitopes from MHC determinants are known in the prior art. Mimotopes can be identified from the use of phage display. Libraries of phages expressing randomly generated amino acid sequences are obtainable from commercial suppliers and are used to identify sequences of amino acids which match the 3-D structure of the hapten-modified MHC determinant. Phages are selected, for instance, by reactivity to a soluble TCR and selected phage are expanded in culture before reapplying to the same selection method.

For a number of pharmaceutical compounds, the immune response in model organisms is described and antibodies can be isolated. Such antibodies can be used to identify peptides from a library which act as a mimotope.

Peptides encompassing class II-restricted or CD1d-restricted peptide epitopes are then modified by inclusion in flanking residues of a 4 amino acid [CST]-x-x-C [SEQ ID NO: 8] or C-x-x-[CST] [SEQ ID NO: 9] motif, in which C stands for cysteine, S for serine, T for threonine and x for any amino acid. In typical embodiments X is not Trp, Tyr or Phe. A preferred motif is C-x-x-C [SEQ ID NO: 10]. Details about the motif, its location and configuration are disclosed in patent applications WO2008017517 and WO2012069568. In brief, the motif can be located on either the amino-terminal or carboxyterminal end of the epitope. The motif can be directly adjacent to the epitope sequence or separated from the first (P1) or the last (P9 for class II-restricted epitopes and P7 for CD1d-restricted peptide epitopes) by 1, 2, 3 or 4 amino acids.

Peptides encompassing class II-restricted or CD1d-restricted peptide epitopes, or both together, can be administered to the animal of choice by any route, preferably together with an adjuvant. In preferred embodiments, peptides are administered by the subcutaneous route after adsorption on aluminum hydroxide. Several injections are made until a minimum cumulative amount of 100 μg is obtained in mice. In larger animals concentrations up to 1 mg are considered. Alternative route of administration include the IV route, intranasal or intratracheal, or intraperitoneal. Alternative adjuvants are envisaged, in particular for CD1d-restricted peptides, for which it may be advantageous to use lipids or glycolipids known to activate NKT cells.

Once immunization with peptides is carried out, the animal may, optionally, be tested for absence of reactivity towards the pharmaceutical compound. In a preferred setting, the compound is administered by the same route as the one contemplated for therapeutic purposes.

Animals are then exposed by natural route to a physiologically relevant dose of the pharmaceutical compounds and the properties of the compound are followed over time.

For evaluation of toxicity, animals can be followed for prolonged periods of time and the relevant toxicity assessment carried out. It should be obvious for those skilled in the art that the animal model of the invention can be used for testing repeated doses over prolonged periods of time, which is advantageous, for instance, when a risk of accumulation in the body may exist.

For evaluation of the pharmacokinetic properties of the pharmaceutical compounds under testing, the present methodology eliminates the most important confounding factor for such testing, namely the specific immune response. It therefore provides an opportunity to carry out several assessments of the pharmacokinetic properties over time, which may vary widely. One example is provided by therapeutic antibodies. The clearance of the antibody will be conditioned essentially by its reactivity with its target, in absence of specific immune response. This could lead to various, mostly unexplored responses of the recipient, such as increased production of the target itself, thereby altering the therapeutic dose required to control the disease process.

The methods of the present invention are suitable for testing a wide range of medicaments for various conditions, including, but not limited to

- medicaments for conditions of the cardiovascular system such as hypertension, arrhythmia, heart failure, angor, diuretics, hypotension and hyperlipidemia
- medicaments for conditions of the digestive tract (incl. nausea and vomiting) such as anti-acids, cholagogues and choleretics, laxatives, anti-diarrheics, anti-inflammatory and antiseptic drugs
- medicaments for conditions of the urogenital system such as benign prostate hypertrophy, impotence
- medicaments for conditions of the respiratory tract such as asthma and COPD, cough, analgesics, non-steroid anti-inflammatory drugs, gout
- medication acting at the CNS level such as hypnotics, antipsychotics, anti-depression, Parkinson, epilepsy, migraine, antihistamine, cholinesterase inhibitors hormones in general
- antibiotics,
- antiviral compounds,
- antifungal compounds,
- antiparasite medicaments,
- anti-tumor compounds.

The following examples illustrate the invention, which should not be considered as limited by such examples.

EXAMPLES

Example 1

Design of a Mimotope Sequence for a Non-Proteic Pharmaceutical Compound

Small chemicals can directly bind to proteins such as albumin or membrane proteins. This binding can result in an immune reaction when such a small chemical binds to a sequence of the protein which is part of an epitope recognized by T cells.

To mimic this type of interaction, functional T cell epitopes, as for instance those presented in the context of MHC class II complexes, can be produced by interacting the chemical with the peptidic sequence, thereby producing a mimotope. Under such a setting, the chemical is attached to an amino acid residue which comes in contact with the TCR, thereby preserving the capacity of the epitope to bind to anchoring residues for class II molecule binding.

An example is the production of antibodies to penicillin, which is driven by activation of class II-restricted T cells, the receptor of which being specific for the epitope as modified by reaction with the betalactam ring of penicillin. Another example is the activation of CD4+ T cells with metal ion-modified epitopes, such as beryllium or nickel.

The beta-lactam ring of penicillin is the target for a nucleophilic attack by free amino groups of proteins and in particular epsilon-amino groups of lysine, leading to covalent amide bonding. Class II-restricted T cell epitopes or CD1d-restricted NKT peptide epitopes containing lysine can form covalent complexes with penicillin. Such epitopes are presented and activate either class II-restricted CD4+ T cells, or CD1d-restricted NKT cells, respectively.

An epitope of the membrane cofactor protein (MCP) is known to be presented in the context of a MHC class II determinant, DRB1*1101. The sequence of this epitope, which corresponds to residues 315-328 of MCP, contains several lysines (PYRYLQRRKKKGK [SEQ ID NO: 1]). Incubation of this epitope with penicillin G results in the substitution of lysine in position 8 of the epitope (underlined). This mimotope is able to activate CD4+ T cells as derived from peripheral CD4+ T cells from patients with immune response to penicillin (Padovan et al. (1997) *Eur. J. Immunol.* 27, 1303-1307).

For the purpose of the methods of the present invention, the mimotope sequence was then modified by addition of a 4-amino acid motif containing an oxido-reductase activity, so as to generate the sequence CPYCVPYRYLQRRKKKGK [SEQ ID NO: 2], which includes an oxido-reductase motif at the aminoterminus, 2 amino acids as a linker (VP), and the sequence of the mimotope.

Administration of a synthetic peptide encompassing the peptide of SEQ ID NO: 2 to a mouse rendered transgenic for expression of the DRB1*1101 human class II molecule suppresses the capacity of the mouse to elicit an immune response towards penicillin.

Example 2

Pharmacokinetic Evaluation of Factor VIII Molecules in Model Animals

Factor VIII replacement therapy is used for the treatment of hemophilia A patients. However, the FVIII t ½ in circulation is only 90 minutes. In the presence of Von Willebrand factor, its physiological chaperon molecule, FVIII t ½ is increased to up to 6 h. The production of FVIII molecules with prolonged t ½ is a long-awaited goal. A number of FVIII molecules with increased T ½ have recently been proposed. These are obtained by either fusion with the Fcgamma part of IgG antibodies to ensure recirculation of FVIII through the FcRN, substitution with PEG molecules, or cross-bridging of FVIII domains to reduce its catabolism. Evaluation of t ½ for such modified FVIII constructs is carried out in animal models. Herein, healthy mice are injected with increasing doses of human FVIII and the persistence of the administered FVIII is assessed over time. However, human FVIII is strongly immunogenic in mice and rapidly elicits an immune response. This also occurs in mice sufficient in (and therefore tolerant to) their own FVIII, as the differences of sequences between mouse and human FVIII are sufficient to elicit an immune response in mouse. The end result is that even after a very limited number of injections, the emergence of murine antibodies towards the administered human FVIII precludes any further testing of pharmacokinetic properties, as the murine antibodies immediately neutralize administered human FVIII.

A synthetic peptide encompassing class II-restricted T cell epitope of human Factor VIII and a CxxC motif CGHC GG FTNMFATWSPSK [SEQ ID NO: 3] is used to immunize healthy mice before human FVIII administration. Four injections of 50 μg of such peptide adsorbed on aluminum hydroxide are made by the subcutaneous route to healthy mice and at weekly intervals. Mice are shown to be tolerant to human FVIII and used for kinetic evaluation of FVIII molecule with prolonged t ½.

Example 3

Prevention of an Immune Response to Human Factor VIII in Non-Inbred Dogs

In animals such as dogs, antibodies are equally raised against human FVIII. Although these antibodies do not neutralize human FVIII, these antibodies have an effect on biological disposal of administered human FVIII to such animal models.

Mice and other rodents are often inbred strains all having the same type of MHC class II molecules.

Other animals such as dogs are outbred and may carry variable MHC class II determinants between animals. In order to set up a reliable experiment, class II HLA mapping should be performed on each animal to assure that the administered peptide is effectively recognized.

However, the absence of polymorphism of the CD1d molecule renders it possible to use a single peptide with an NKT peptide epitope and a redox motif sequence to switch off the immune response towards the antigen in all animals of the species, also in outbred strains.

Dogs are immunized with 250 μg of a human factor VIII CD1d-restricted epitope by subcutaneous administration of a synthetic peptide adsorbed on alum, the sequence of which is CPYC-VP-QTLHKFILLFA [SEQ ID NO:4].

This peptides contains human factor VIII amino acid sequence 190-200 (QTLHKFILLFA [SEQ ID NO:5]), with CD1d anchoring residues in positions 1, 4 and 7 (underlined), a linker of 2 amino acids (VP) and a thioreductase motif at the amino terminal side.

A total of 4 injections with peptide adsorbed on aluminum hydroxide is carried out with an interval of 10 days.

Dogs are then treated by intravenous administration of full-length human factor VIII and the pharmacokinetic properties of human factor VIII are then evaluated upon repeated injection of human factor VIII.

Example 4

Assessment of Toxicity of Anti-TNF Alpha Antibodies

Administration of humanized monoclonal antibodies in patients suffering from chronic inflammatory diseases such as rheumatoid arthritis is nowadays common practice. Although clinical improvement is generally observed, long-term administration of such therapeutic antibodies leads to severe side effects and complications. These effects have been essentially identified in patients treated on longer terms with the therapeutic antibody, and were not predicted from preclinical animal toxicology evaluation. The main reason for this is related to the high immunogenicity of such therapeutic antibodies in animal models, mice or rats in particular.

An H-2b-restricted T cell epitope for C57BL/6 mouse is found in the heavy chain of the Humira™ anti-TNFalpha antibody: YYAPWCNN [SEQ ID NO: 6]

A peptide comprising this epitope and a redox motif sequence (CPYCVP YYAPWCNN [SEQ ID NO:7]) is administered to wild type non-rheumatoid C57BL/6 mice at a dose of 50 μg per injection made by the subcutaneous route, 4 times at an interval of one week.

Mice are then treated by intravenous administration of the anti-TNF-alpha antibody. In the absence of immune response towards the antibody, injections can be repeated and the effects of such administration can be evaluated on the long term.

Example 5

Evaluation of the Toxicity of Repeated Administration of a Pegylated Derivative of Factor VIII Pharmaceutical compounds often have a reduced t ½ and various attempts to prolong their activity have been proposed. Thus, substitution with ethylene glycol residues is currently used for a number of such pharmaceutical compounds. Although this is considered a safe procedure, some reports identify accumulation of pegylated molecules within scavenger cells such as macrophages. In fact, PEG substitution increases t ½ by masking residues involved in the clearance of pharmaceutical compounds from the circulation. It also prevents digestion by the proteasome and as such can increase cell accumulation. The hallmark of such accumulation is usually the appearance of foamy macrophages.

Pegylated proteins are essentially eliminated by the kidney and by the liver. Reports have shown vacuole accumulation in renal tubular epithelial cells as well as in liver Kupffer cells. These concerns about the safety of PEG-substituted pharmaceutical compounds require long-term evaluation in suitable animal models (Zhang et al. (2014) *Biol. Pharm. Bull.* 37, 335-339).

This evaluation is severely limited by the fact that PEGylated proteins can be immunogenic. First, PEG itself is reported to elicit an IgM immune response, which can trigger activation of the complement pathway, opsonization and removal by Kupffer cells. Besides, the immunogenicity of the pharmaceutical compound itself, though reduced by pegylation, is not eliminated. For these 2 reasons, it is advantageous to evaluate these phenomena.

The production of IgM antibodies to PEG moieties is T cell independent and can therefore not be eliminated by the current invention. By contrast, preventing any immune response towards the pharmaceutical compound itself, already prevents part of the immune response against the pharmaceutical compound and represents a significant improvement and allow testing the toxicity of PEG over long periods of time. The IgM response towards PEG does not induce memory and is not problematic for long-term toxicity studies.

Healthy mice are immunized according to the procedure described in Example 2 and then treated by regular administration of pegylated human FVIII over long periods of time. At discrete points in time, mice are sacrificed and the extent of vacuolization of kidney tubular cells epithelium and that of liver Kupffer cells is examined.

The invention claimed is:

1. A method for determining toxicity, pharmacokinetics, half life time, tissue uptake, or metabolism of a polypeptide of interest in a non-human animal, the method comprising the steps of:
   (a) administering a fusion polypeptide to the non-human animal in a sufficient amount to suppress the non-human animal's ability to mount an immune response against the polypeptide of interest, wherein the fusion polypeptide is administered subcutaneously, intraperitoneally, or intravenously;

(b) administering the polypeptide of interest to the non-human animal; and (c) determining the toxicity, pharmacokinetics, half life time, tissue uptake, or metabolism of the polypeptide of interest, wherein the polypeptide of interest comprises an MHC class II-restricted T cell epitope, and wherein the fusion polypeptide consists of 12 to 50 amino acid residues comprising (i) an oxidoreductase motif of CXXC (SEQ ID NO: 10), (ii) an amino acid sequence comprising the MHC class II-restricted T cell epitope of the polypeptide of interest, and (iii) a linker of between 0 and 4 amino acids separating the oxidoreductase motif and the amino acid sequence comprising the MHC class II-restricted T cell epitope of the polypeptide of interest, wherein the oxidoreductase motif is located on either the amino-terminal or carboxy-terminal side of the amino acid sequence comprising the MHC class II-restricted T cell epitope.

2. The method according to claim 1, wherein the polypeptide of interest is the adalimumab anti-TNF alpha antibody, and the fusion polypeptide has the sequence of CPY-CVPYYAPWCNN (SEQ ID NO: 7).

3. The method according to claim 1, wherein the non-human animal is not a primate.

4. The method according to claim 1, wherein the non-human animal is a rodent.

5. The method according to claim 1, wherein the non-human animal is an outbred animal.

6. The method of claim 1, wherein the fusion polypeptide consist of the oxidoreductase motif, the sequence comprising the epitope of the polypeptide of interest, and the linker.

7. The method of claim 1, which comprises determining the half life time of the polypeptide of interest.

8. The method of claim 1, which comprises determining the toxicity of the polypeptide of interest.

9. A method for determining toxicity, pharmacokinetics, half life time, tissue uptake, or metabolism of a polypeptide of interest in a non-human animal, the method comprising the steps of:
   (a) administering the polypeptide of interest to the non-human animal, wherein the non-human animal has been administered subcutaneously, intraperitoneally, or intravenously a sufficient amount of a fusion polypeptide prior to (a) to suppress the non-human animal's ability to mount an immune response against the polypeptide of interest; and
   (b) determining the toxicity, pharmacokinetics, half life time, tissue uptake, or metabolism of the polypeptide of interest,
   wherein the polypeptide of interest comprises an MHC class II-restricted T cell epitope, and wherein the fusion polypeptide consists of 12 to 50 amino acid residues comprising (i) an oxidoreductase motif of CXXC (SEQ ID NO: 10), (ii) an amino acid sequence comprising the MHC class II-restricted T cell epitope of the polypeptide of interest, and (iii) a linker of between 0 and 4 amino acids separating the oxidoreductase motif and the amino acid sequence comprising the MHC class II-restricted T cell epitope of the polypeptide of interest, wherein the oxidoreductase motif is located on either the amino-terminal or carboxy-terminal side of the amino acid sequence comprising the MHC class II-restricted T cell epitope.

10. The method according to claim 9, wherein the polypeptide of interest is the adalimumab anti-TNF alpha antibody, and the fusion polypeptide has the sequence of CPYCVPYYAPWCNN (SEQ ID NO: 7).

11. The method according to claim 9, wherein the non-human animal is not a primate.

12. The method according to claim 9, wherein the non-human animal is a rodent.

13. The method according to claim 9, wherein the non-human animal is an outbred animal.

14. The method of claim 9, wherein the fusion polypeptide consist of the oxidoreductase motif, the sequence comprising the epitope of the polypeptide of interest, and the linker.

15. The method of claim 9, which comprises determining the half life time of the polypeptide of interest.

16. The method of claim 9, which comprises determining the toxicity of the polypeptide of interest.

17. The method of claim 1, wherein the fusion polypeptide comprises a linker of between 1 and 4 amino acids separating the oxidoreductase motif and the amino acid sequence comprising the MHC class II-restricted T cell epitope.

18. The method of claim 9, wherein the fusion polypeptide comprises a linker of between 1 and 4 amino acids separating the oxidoreductase motif and the amino acid sequence comprising the MHC class II-restricted T cell epitope.

* * * * *